US007128823B2

United States Patent
Yang et al.

(10) Patent No.: US 7,128,823 B2
(45) Date of Patent: Oct. 31, 2006

(54) ANOLYTE FOR COPPER PLATING

(75) Inventors: Michael X. Yang, Palo Alto, CA (US); Nicolay Y. Kovarsky, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 311 days.

(21) Appl. No.: 10/616,044

(22) Filed: Jul. 8, 2003

(65) Prior Publication Data
US 2004/0016647 A1    Jan. 29, 2004

Related U.S. Application Data

(63) Continuation-in-part of application No. 10/268,284, filed on Oct. 9, 2002.

(60) Provisional application No. 60/398,345, filed on Jul. 24, 2002.

(51) Int. Cl.
*C25D 3/38* (2006.01)
*C25B 9/00* (2006.01)

(52) U.S. Cl. .................. 205/296; 205/291; 204/252; 204/264; 204/295

(58) Field of Classification Search ............. 205/291, 205/296, 157, 96; 204/252, 263, 264, 295, 204/296
See application file for complete search history.

(56) References Cited

U.S. PATENT DOCUMENTS

| 4,296,672 A | 10/1981 | Inhofer |
| 4,469,564 A | 9/1984 | Okinaka et al. |
| 4,632,851 A | 12/1986 | Broadbent et al. |
| 4,840,820 A | 6/1989 | Schultz et al. |
| 5,071,591 A | 12/1991 | Sheridan |
| 5,162,079 A | 11/1992 | Brown |
| 5,224,504 A | 7/1993 | Thompson et al. |
| 5,252,196 A | 10/1993 | Sonnenberg et al. |
| 5,287,237 A | 2/1994 | Kitada et al. |

(Continued)

FOREIGN PATENT DOCUMENTS

JP    7 14811    1/1995

(Continued)

OTHER PUBLICATIONS

PCT Notification Concerning Transmittal of International Preliminary Report on Patentability dated Jan. 19, 2006 for PCT/US04/022183.

(Continued)

*Primary Examiner*—Nam Nguyen
*Assistant Examiner*—Luan V. Van
(74) *Attorney, Agent, or Firm*—Patterson & Sheridan LLP

(57) ABSTRACT

Embodiments of the invention provide a method for plating copper into features formed on a semiconductor substrate. The method includes positioning the substrate in a plating cell, wherein the plating cell includes a catholyte volume containing a catholyte solution, an anolyte volume containing an anolyte solution, an ionic membrane positioned to separate the anolyte volume from the catholyte volume, and an anode positioned in the anolyte volume. The method further includes applying a plating bias between the anode and the substrate, plating copper ions onto the substrate from the catholyte solution, and replenishing the copper ions plated onto the substrate from the catholyte solution with copper ions transported from the anolyte solution via the ionic membrane, wherein the catholyte solution has a copper concentration of greater than about 51 g/L.

31 Claims, 5 Drawing Sheets

U.S. PATENT DOCUMENTS

| | | |
|---|---|---|
| 5,435,903 A | 7/1995 | Oda et al. |
| 5,482,680 A | 1/1996 | Wilkinson et al. |
| 5,486,264 A | 1/1996 | Ghandour |
| 5,489,341 A | 2/1996 | Bergman et al. |
| 5,516,418 A | 5/1996 | Doss et al. |
| 5,573,023 A | 11/1996 | Thompson et al. |
| 5,597,460 A | 1/1997 | Reynolds |
| 5,620,581 A | 4/1997 | Ang |
| 5,643,456 A | 7/1997 | Smith et al. |
| 5,656,386 A | 8/1997 | Scherer et al. |
| 5,705,050 A | 1/1998 | Sampson et al. |
| 5,714,521 A | 2/1998 | Kedem et al. |
| 5,731,678 A | 3/1998 | Zila et al. |
| 5,744,019 A | 4/1998 | Ang |
| 5,785,833 A | 7/1998 | Vaughan |
| 5,837,120 A | 11/1998 | Forand et al. |
| 5,883,762 A | 3/1999 | Calhoun et al. |
| 5,984,341 A | 11/1999 | Kass et al. |
| 5,996,241 A | 12/1999 | Thompson et al. |
| 6,014,817 A | 1/2000 | Thompson et al. |
| 6,024,856 A | 2/2000 | Haydu et al. |
| 6,080,291 A | 6/2000 | Woodruff et al. |
| 6,090,260 A | 7/2000 | Inoue et al. |
| 6,099,702 A | 8/2000 | Reid et al. |
| 6,099,711 A * | 8/2000 | Dahms et al. ............... 205/101 |
| 6,099,712 A | 8/2000 | Ritzdorf et al. |
| 6,113,771 A * | 9/2000 | Landau et al. ............... 205/123 |
| 6,126,798 A | 10/2000 | Reid et al. |
| 6,132,857 A | 10/2000 | Champenois et al. |
| 6,136,163 A | 10/2000 | Cheung et al. |
| 6,156,167 A | 12/2000 | Patton et al. |
| 6,167,893 B1 | 1/2001 | Taatjes et al. |
| 6,179,983 B1 | 1/2001 | Reid et al. |
| 6,197,181 B1 | 3/2001 | Chen |
| 6,228,231 B1 | 5/2001 | Uzoh |
| 6,228,232 B1 | 5/2001 | Woodruff et al. |
| 6,248,222 B1 | 6/2001 | Wang |
| 6,251,255 B1 | 6/2001 | Copping |
| 6,254,742 B1 | 7/2001 | Hanson et al. |
| 6,261,433 B1 * | 7/2001 | Landau ........................ 205/96 |
| 6,267,853 B1 | 7/2001 | Dordi et al. |
| 6,270,635 B1 | 8/2001 | Woo |
| 6,273,110 B1 | 8/2001 | Davis et al. |
| 6,280,291 B1 | 8/2001 | Gromko et al. |
| 6,280,582 B1 | 8/2001 | Woodruff et al. |
| 6,290,833 B1 | 9/2001 | Chen |
| 6,309,981 B1 | 10/2001 | Mayer et al. |
| 6,319,387 B1 | 11/2001 | Krishnamoorthy et al. |
| 6,322,674 B1 | 11/2001 | Berner et al. |
| 6,322,678 B1 | 11/2001 | Woodruff et al. |
| 6,334,937 B1 | 1/2002 | Batz, Jr. et al. |
| 6,347,837 B1 | 2/2002 | Watson et al. |
| 6,368,475 B1 | 4/2002 | Hanson et al. |
| 6,374,837 B1 | 4/2002 | Scranton et al. |
| 6,379,522 B1 * | 4/2002 | Landau et al. ............... 205/157 |
| 6,383,352 B1 | 5/2002 | Shyu et al. |
| 6,391,166 B1 | 5/2002 | Wang |
| 6,395,101 B1 | 5/2002 | Scranton et al. |
| 6,395,152 B1 | 5/2002 | Wang |
| 6,409,892 B1 | 6/2002 | Woodruff et al. |
| 6,423,642 B1 | 7/2002 | Peace et al. |
| 6,432,821 B1 | 8/2002 | Dubin et al. |
| 6,436,249 B1 | 8/2002 | Patton et al. |
| 6,440,295 B1 | 8/2002 | Wang |
| 6,503,375 B1 | 1/2003 | Maydan et al. |
| 6,518,184 B1 | 2/2003 | Chambers et al. |
| 6,521,102 B1 | 2/2003 | Dordi |
| 6,527,920 B1 * | 3/2003 | Mayer et al. ............... 204/237 |
| 6,551,479 B1 | 4/2003 | Graham et al. |
| 6,551,487 B1 | 4/2003 | Reid et al. |
| 6,558,518 B1 | 5/2003 | Sendai |
| 6,569,299 B1 | 5/2003 | Reid et al. |
| 6,576,110 B1 | 6/2003 | Maydan |
| 6,586,342 B1 | 7/2003 | Mayer et al. |
| 6,589,401 B1 | 7/2003 | Patton et al. |
| 6,589,874 B1 | 7/2003 | Andricacos et al. |
| 6,592,736 B1 | 7/2003 | Fulton et al. |
| 6,736,952 B1 | 5/2004 | Emesh et al. |
| 6,740,221 B1 | 5/2004 | Cheung et al. |
| 6,773,571 B1 | 8/2004 | Mayer et al. |
| 6,790,773 B1 | 9/2004 | Drewery et al. |
| 6,800,187 B1 | 10/2004 | Reid et al. |
| 6,884,335 B1 | 4/2005 | Webb et al. |
| 6,964,792 B1 | 11/2005 | Mayer |
| 2001/0015321 A1 * | 8/2001 | Reid et al. .................. 205/103 |
| 2001/0032788 A1 * | 10/2001 | Woodruff et al. ........... 205/687 |
| 2001/0052465 A1 * | 12/2001 | Dordi et al. .................. 205/95 |
| 2002/0011415 A1 | 1/2002 | Hey |
| 2002/0033340 A1 | 3/2002 | Cheung et al. |
| 2002/0063097 A1 | 5/2002 | Fukunaga et al. |
| 2002/0074233 A1 | 6/2002 | Ritzdorf et al. |
| 2002/0189950 A1 | 12/2002 | Genders |
| 2002/0195352 A1 | 12/2002 | Mayer |
| 2003/0000850 A1 * | 1/2003 | Horkans et al. ............. 205/775 |
| 2003/0010640 A1 | 1/2003 | Kholodenko |
| 2003/0057098 A1 * | 3/2003 | Sendai et al. ............... 205/143 |
| 2003/0116445 A1 | 6/2003 | Sun et al. |
| 2003/0159937 A1 | 8/2003 | Gandikota et al. |
| 2004/0016636 A1 | 1/2004 | Yang |
| 2004/0016637 A1 | 1/2004 | Yang et al. |
| 2004/0016647 A1 | 1/2004 | Yang et al. |
| 2004/0074761 A1 | 4/2004 | Herchen et al. |
| 2004/0074762 A1 | 4/2004 | Keigler et al. |
| 2004/0118694 A1 | 6/2004 | Yang et al. |
| 2004/0134775 A1 | 7/2004 | Yang et al. |
| 2004/0149573 A1 | 8/2004 | Herchen |
| 2004/0192066 A1 | 9/2004 | Lubomirsky et al. |
| 2004/0195110 A1 | 10/2004 | Srinivasan et al. |
| 2004/0200725 A1 | 10/2004 | Yahalom et al. |
| 2004/0206628 A1 | 10/2004 | Lumbomirsky et al. |
| 2004/0209414 A1 | 10/2004 | Mok |
| 2004/0217005 A1 | 11/2004 | Yang et al. |

FOREIGN PATENT DOCUMENTS

| | | |
|---|---|---|
| JP | 9 293658 | 11/1997 |
| JP | 10 177988 | 6/1998 |
| JP | 10 242110 | 9/1998 |
| JP | 11 162905 | 6/1999 |
| JP | 11 186210 | 7/1999 |
| WO | WO-98/27585 | 6/1998 |
| WO | WO 2001/096632 A3 | 12/2001 |
| WO | WO 2004/003410 A1 | 1/2004 |
| WO | WO 2005/007933 A1 | 1/2005 |

OTHER PUBLICATIONS

PCT Written Opinion of the International Searching Authority dated Jan. 19, 2006 for PCT/US04/022183.

Colombo; "Wafer Back Surface Film Removal," Central R&D, SGS-THOMSON Microelectronics, Agate Italy, no date.

Pitney, "Ney Contact Manual" Oct. 1974.

Semitool Product Catalog (on-line) Oct. 27, 1998.

Singer, "Copper Has Enormous Benefits When Compared to Aluminum, but its Implementation Requires Some Fundamental Changes in Process Technologies," Semiconductor International Jun. 1998.

Singer, "Wafer Processing," Semiconductor International Jun. 1998.

PCT International Search Report from International Application No. PCT/US 2004/022183, dated Oct. 15, 2004.

International Search Report dated Aug. 22, 2005 regarding International Application NO. PCT/US2005/016123.

* cited by examiner

ANOLYTE FOR COPPER PLATING

CROSS-REFERENCE TO RELATED APPLICATIONS

This application is a Continuation In Part Application of U.S. patent application Ser. No. 10/268,284, filed Oct. 9, 2002, which claims priority to U.S. Provisional Patent Application Ser. No. 60/398,345, filed Jul. 24, 2002, both of which are hereby incorporated by reference in their entirety.

BACKGROUND OF THE INVENTION

1. Field of the Invention

Embodiments of the present invention generally relate to a plating cell having isolated catholyte and anolyte regions, wherein the isolated regions are separated from each other by an ionic membrane. Further, embodiments of the invention relate to the chemistries used in the respective anolyte and catholyte chambers of the plating cell having the isolated regions.

2. Description of the Related Art

Metallization of sub-quarter micron sized features is a foundational technology for present and future generations of integrated circuit manufacturing processes. More particularly, in devices such as ultra large scale integration-type devices, i.e., devices having integrated circuits with more than a million logic gates, the multilevel interconnects that lie at the heart of these devices are generally formed by filling high aspect ratio, i.e., greater than about 4:1, interconnect features with a conductive material, such as copper or aluminum. Conventionally, deposition techniques such as chemical vapor deposition (CVD) and physical vapor deposition (PVD) have been used to fill these interconnect features. However, as the interconnect sizes decrease and aspect ratios increase, void-free interconnect feature fill via conventional metallization techniques becomes increasingly difficult. Therefore, plating techniques, i.e., electrochemical plating (ECP) and electroless plating, have emerged as promising processes for void free filling of sub-quarter micron sized high aspect ratio interconnect features in integrated circuit manufacturing processes.

In a conventional ECP process, for example, sub-quarter micron sized high aspect ratio features formed into the surface of a substrate (or a layer deposited thereon) may be efficiently filled with a conductive material, such as copper. ECP plating processes are generally two stage processes, wherein a seed layer is first formed over the surface features of the substrate, and then the surface features of the substrate are exposed to an electrolyte solution, while an electrical bias is applied between the seed layer and a copper anode positioned within the electrolyte solution. The electrolyte solution generally contains ions to be plated onto the surface of the substrate, and therefore, the application of the electrical bias causes these ions to be urged out of the electrolyte solution and to be plated onto the biased seed layer.

Conventional electrochemical plating cells generally utilize an overflow weir-type plater containing a plating solution, which is also generally termed a catholyte herein. The substrate is positioned at the top of the weir during plating and an electrical plating bias is applied between the substrate and an anode positioned on a lower portion of the plating solution. This bias causes metal ions in the plating solution to go through a reduction that causes the ions to be plated on the substrate. However, one challenge associated with conventional plating cells is that the plating solution contains additives that are configured to control the plating process, and these additives are known to react with the anode during plating processes. This reaction with the anode causes the additives to breakdown, which generally renders the additives ineffective. Further, when the additives breakdown and are no longer able to facilitate process control, then the additives essentially become contaminants in the plating solution.

Additionally, other conventional plating cells have implemented a porous membrane into the plating cell that operates, to separate an anolyte solution (discussed herein) from the plating solution or catholyte. The intent of this configuration is to prevent additives in the plating solution from contacting the anode and depleting or degrading. Conventional applications of the porous membrane include microporous chemical transport barriers, which are supposed to limit chemical transport of most species, while allowing migration of anion and cation species, and hence passage of current. Examples of conventional membranes include porous glass, porous ceramics, silica aerogels, organic aerogels, porous polymeric materials, and filter membranes. Specific membranes include carbon filter layers, Kynar layers, or polypropylene membranes.

However, in similar fashion to weir-type plating cells, conventional cells that use porous membranes to isolate the catholyte from the anolyte have also been shown to leak additives through the membrane, which allows for the additives to again contact the anode and deplete. Additionally, conventional membranes present challenges to maintaining plating metal ion concentrations in the catholyte solutions. More particularly, conventional membranes generally allow several different types of ions from the plating solution to pass therethrough, and as such, the plating metal ion transport is hindered, as these ions must compete with the other ions to pass through the membrane. As such, conventional plating cells that attempt to isolate the catholyte from the anolyte are generally ineffective in preventing plating solution additives from reaching the anode, and further, generate plating metal ion diffusion challenges.

Another challenge associated with conventional plating cells that utilize a membrane to separate the anolyte compartment (the compartment adjacent the anode and below the membrane, i.e., where the anolyte solution comes into contact with the anode) from the catholyte compartment (the compartment above the membrane, which is generally a plating solution that contacts the substrate for plating) is that the anolyte makeup causes copper sulfate precipitation, which is detrimental to plating. Further, conventional membrane and anolyte configurations suffer from poor or uncontrollable copper transport parameters, which generates inconsistent plating results. Conventional plating cells have attempted to address this situation via use of membranes that are known to be poor copper conductors, and then bleeding a portion of the inherently copper rich anolyte into the catholyte to make up for the poor copper transfer. Although this process may be effective for increasing the copper concentration in the catholyte, it also suffers from control problems, such as copper concentration fluctuation and concentration control of the catholyte, since anolyte is continually being added thereto. Additional challenges presented by convention anolyte concentrations include undesirable hydrogen transport through the membrane from the anolyte to the catholyte, which results in an increased sulfuric acid concentration.

Therefore, there is a need for a plating cell and chemistry configuration configured to minimize additive breakdown at the anode, while allowing for adequate metal ion permeability from the anolyte to the catholyte.

SUMMARY OF THE INVENTION

Embodiments of the invention generally provide a plating cell having separate anolyte and catholyte chambers. The respective chambers are separated by an ionic membrane configured to efficiently transfer copper ions therethrough from the anolyte chamber to the catholyte chamber, while also minimizing or controlling the transfer of hydrogen ions and water therethrough. Further, the catholyte of the invention is configured to facilitate between about 90% and about 100% of copper ion transfer through the membrane, while preventing copper sulfate and copper hydroxide precipitation and minimizing hydrogen ion transfer.

Embodiments of the invention may further provide a method for plating metal onto a substrate. The method includes positioning the substrate in a catholyte solution contained in a catholyte chamber of a plating cell, wherein the catholyte solution includes an acid source at a concentration of between about 5 g/L and about 15 g/L, a copper source at a concentration of between about 0.8M and about 0.9M, and chlorine ions at a concentration of between about 25 ppm and about and about 75 ppm. The method further includes applying a plating bias between the substrate and an anode positioned in an anolyte chamber of the plating cell, the anolyte chamber being separated from the catholyte chamber by an ionic membrane and being supplied with an anolyte solution comprising a copper source having a concentration of greater than about 51 g/L.

Embodiments of the invention may further provide a method for plating copper into features formed on a semiconductor substrate. The method includes positioning the substrate in a plating cell, wherein the plating cell includes a catholyte volume containing a catholyte solution, an anolyte volume containing an anolyte solution, an ionic membrane positioned to separate the anolyte volume from the catholyte volume, and an anode positioned in the anolyte volume. The method further includes applying a plating bias between the anode and the substrate, plating copper ions onto the substrate from the catholyte solution, and replenishing the copper ions plated onto the substrate from the catholyte solution with copper ions transported from the anolyte solution via the ionic membrane, wherein the catholyte solution has a copper concentration of greater than about 51 g/L.

Embodiments of the invention may further provide a method for electrochemically plating copper onto features of a semiconductor substrate. The method includes positioning the substrate in a plating cell having a catholyte solution volume, an anolyte solution volume, and an ionic membrane separating catholyte solution volume from the anolyte solution volume, contacting the substrate with a catholyte solution, and applying an electrical bias between the substrate and an anode positioned in the anolyte volume, the electrical bias being sufficient to plate copper ions from the catholyte solution onto the substrate. The method further includes replenishing copper ions plated from the catholyte solution via transfer of copper ions from the anolyte solution through the ionic membrane, the anolyte solution having a pH of between about 2 and about 4.8 and a copper ion concentration of between about 0.1M and about 2M.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The present invention generally provides an electrochemical plating cell configured to plate metal onto semiconductor substrates using a small volume cell, i.e., a cell weir volume that houses less than about 4 liters of electrolyte in the cell itself, preferably between about 1 and 3 liters, and potentially between about 2 and about 8 liters of electrolyte solution in an adjacent fluidly connected supply tank. These small volumes of fluid required to operate the cell of the invention allow the electroplating cell to be used for a predetermined range of substrates, i.e., 100–200, and then the solution may be discarded and replaced with new solution. The electrochemical plating cell is generally configured to fluidly isolate an anode of the plating cell from a cathode or plating electrode of the plating cell via a cation membrane positioned between the substrate being plated and the anode of the plating cell. Additionally, the plating cell of the invention is generally configured to provide a first fluid solution to an anode compartment, i.e., the volume between the upper surface of the anode and the lower surface of the membrane, and a second fluid solution (a plating solution) to the cathode compartment, i.e., the volume of fluid positioned above the upper membrane surface. The anode of the plating cell generally includes a plurality of slots formed therein, the plurality of slots being positioned parallel to each other and are configured to remove a concentrated hydrodynamic Newtonian fluid layer from the anode chamber surface during plating processes. A membrane support having a plurality of slots or channels formed in a first side of the assembly, along with a plurality of bores formed into a second side of the membrane support, wherein the plurality of bores are in fluid communication with the slots on the opposing side of the membrane support.

Figure 1:
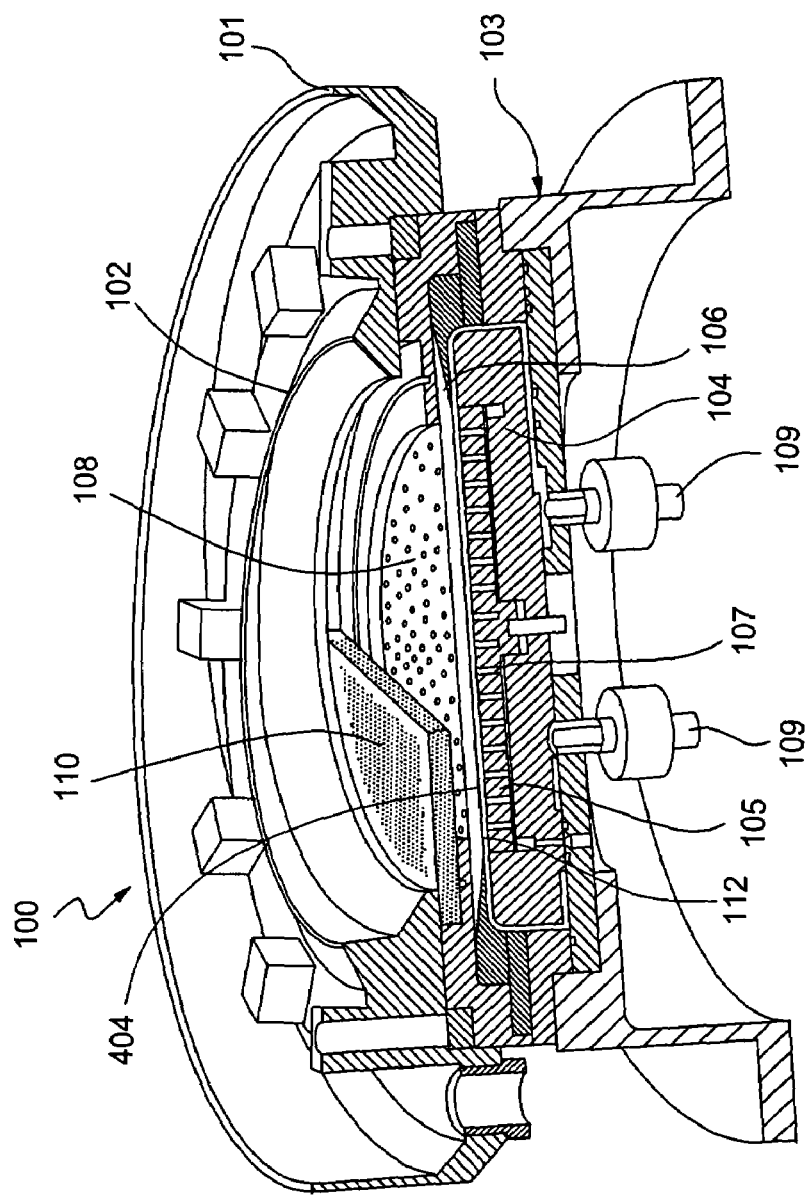
FIG. 1 illustrates a partial sectional perspective view of an exemplary electrochemical plating slim cell of the invention.

FIG. 1 illustrates a perspective and partial sectional view of an exemplary electrochemical plating cell 100 of the invention. The plating cell 100 generally includes an outer basin 101 and an inner basin 102 positioned within the outer basin 101. The inner basin 102 is generally configured to contain a plating solution that is used to plate a metal, e.g., copper, onto a substrate during an electrochemical plating process. During the plating process, the plating solution is generally continuously supplied to the inner basin 102 (at about 1 gallon per minute for a 10 liter plating cell, for example), and therefore, the plating solution continually overflows the uppermost point of the inner basin 102 and runs into the outer basin 101. The overflow plating solution is then collected by the outer basin 101 and drained therefrom for recirculation into the inner basin 102. As illustrated in FIG. 1, the plating cell 100 is generally positioned at a tilt angle, i.e., a frame member 103 of the plating cell 100 is generally elevated on one side such that the components of the plating cell 100 are tilted between about 3° and about 30°. Therefore, in order to contain an adequate depth of the plating solution within the inner basin 102 during plating operations, the uppermost portion of the inner basin 102 may be extended upward on one side of the plating cell 100, such that the uppermost point of the inner basin 102 is generally horizontal and allows for contiguous overflow of the plating solution supplied thereto around the perimeter of the inner basin 102.

The frame member 103 of the plating cell 100 generally includes an annular base member 104 secured to the frame member 103. Since the frame member 103 is elevated on one side, the upper surface of the base member 104 is generally tilted from the horizontal at an angle that corresponds to the angle of the frame member 103 relative to a horizontal position. The base member 104 includes an annular or disk shaped recess formed therein, the annular recess being configured to receive a disk shaped anode 105. The anode 105 may be a soluble anode, such as a pure copper anode, a doped copper anode (doped with phosphorous, for example), or another soluble anode known in the plating art, or alternatively, an insoluble anode, such as a platinum anode, platinized titanium anode, or other inert or insoluble anode known in the plating art may be used. The base member 104 further includes a plurality of fluid inlets/drains 109 positioned on a lower surface thereof. Each of the fluid inlets/drains 109 are generally configured to individually supply or drain a fluid to or from either the anode compartment or the cathode compartment of the plating cell 100. The anode 105 generally includes a plurality of slots 107 formed therethrough, wherein the slots 107 are generally positioned in parallel orientation with each other across the surface of the anode 105. The parallel orientation allows for dense fluids generated at the anode surface to flow downwardly across the anode surface and into one of the slots 107. The plating cell 100 further includes a membrane support assembly 106. The membrane support assembly 106 is generally secured at an outer periphery thereof to the base member 104, and includes an interior region 108 configured to allow fluids to pass therethrough via a sequence of oppositely positioned slots and bores. The membrane support assembly 106 may include an o-ring type seal positioned near a perimeter of the membrane support assembly 106, wherein the seal is configured to prevent fluids from traveling from one side of a membrane 112 secured on the membrane support assembly 106 to the other side of the membrane 112.

The membrane 112 generally operates to fluidly isolate the anode chamber from the cathode chamber of the plating cell 100. The membrane 112 is generally an ionic membrane. The ion membrane generally includes fixed negatively charged groups, such as $SO_3^-$, $COO^-$, $HPO_2^-$, $SeO_3^-$, $PO_3^{2-}$, or other negatively charged groups amenable to plating processes. The membrane 112 allows a particular type of ions to travel through the membrane, while preventing another type of ion from traveling or passing through the membrane 112. More particularly, the membrane 112 may be a cationic membrane that is configured to allow positively charged copper ions ($Cu^{2+}$) to pass therethrough, i.e., to allow copper ions to travel from the anode 105 in the anolyte solution through the membrane 112 into the catholyte solution, where the copper ions may then be plated onto the substrate. Further, the cationic membrane may be configured to prevent passage of negatively charged ions and electrically neutral species in the solution, such as the ions that make up the plating solution and catholyte additives. It is desirable to prevent these catholyte additives from traveling through the membrane 112 and contacting the anode 105, as the additives are known to break down upon contacting the anode 105. More particularly, membranes with negatively charged ion groups like $SO_3^-$ etc. not only to facilitate Cu ions transport from the anolyte to the catolyte, but also to prevent penetration of accelerators to the anode 105. The accelerator is generally negatively charged organic ion: $^-SO_3^-$—$C_3H_6$—S—S—$C_3H_6$—$SO_3^-$, so it can't penetrate into or through the cationic membrane. This is important, as consumption of accelerators on copper anodes on conventional plating apparatuses without the ionic membrane is very high.

Membrane 112 may be a Nafion®-type membrane manufactured by Dupont Corporation. Nafion® is an example of a poly (tetrafluoroethylene) based ionomer. Nafion® has several desirable characteristics for electrochemical plating applications, such as its thermal and chemical resistance, ion-exchange properties, selectivity, mechanical strength, and insolubility in water. Nafion® is also a cationic membrane based on a fluorized polymer matrix. Because of fluorized matrix, Nafion® exhibits excellent chemical stability, even in concentrated basic solutions. More particularly, Nafion® is a perfluorinated polymer that contains small proportions of sulfonic or carboxylic ionic functional groups, and has shown to be effective in transmitting metal ions (copper ions in the present embodiment) therethrough, even at low plating current densities. Specifically, Nafion® membranes have shown to be effective at transmitting between about 94% and about 98% of copper ions therethrough at plating current densities of between about 5 mA/cm$^2$ and about 20 mA/cm$^2$. Additionally, at current densities of between about 20 mA/cm$^2$ and about 60 mA/cm$^2$, Nafion® transmits between about 97% and about 93% of copper ions therethrough. The above noted transmission percentages were observed using a copper sulfate solution having a ph of about 3.4. Nafion's® general chemical structure (illustrated below), illustrates where X is either a sulfonic or carboxylic functional group and M is either a metal cation in the neutralized form or an H+ in the acid form. As a result of electrostatic interactions, the ionic groups that form Nafion® tend to aggregate to form tightly packed regions referred to as clusters. The presence of these electrostatic interactions between the ions and the ion pairs enhance the intermolecular forces and thereby exert a significant effect on the properties of the parent polymer, which makes Nafion®, or other membranes having similar physical and/or operational characteristics, a desirable ionic membrane for use in electrochemical plating cells having separated anolyte and catholyte chambers.

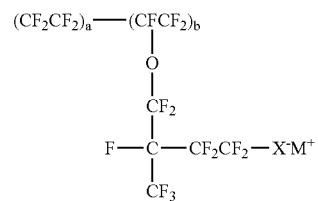

Other membranes that may be used in embodiments of the invention include various cationic and anionic membranes. For example, ionic membranes manufactured by Tokuyama of Japan, i.e., CMX-SB ionic membranes that are based on a polydivinilbenzol matrix, may be used to isolate a catholyte solution from an anolyte solution in an electrochemical plating cell. CMX-SB membranes have shown to be effective in transmitting copper ions while preventing organic plating additives from transmitting therethrough. Additionally, CMX-SB membranes have shown acceptable resistance to transmission of positive hydrogen ions. More particularly, CMX membranes have been shown to transmit above about 92% of copper ions at a current density of about 10 mA/cm$^2$, and above about 98% at a current density of about 60 mA/cm$^2$. Ionics CR-type membranes from Ionics Inc. have also shown to be able to transmit above about 92% of copper ions at about 10 mA/cm$^2$ and above about 88% of copper ions at about 60 mA/cm$^2$.

With regard to other properties of the above noted membranes (Ionics, CMX, and Nafion®), each exhibit relatively high conductivity, i.e., about 41.2, 35.3, and 24.2 ohm cm$^2$ at IOmA/cm$^2$ for Ionics, Neosepta and Nafion®, respectively. Additional properties of the respective membranes are illustrated in Table 1.

TABLE 1

| Membrane | Cu$^{2+}$ transfer, % | Resistance ohm cm2 | Cu/Acid Ration Deviation, % |
|---|---|---|---|
| Ionics | 90–95 | 53 | 4% |
| Nafion | 95–98 | 36 | 2% |
| CMX | 97–98 | 47 | 1% |

Vicor membranes may also be used to advantage in the plating cell of the invention. Other membranes that may be used in the plating cell of the invention include Neosepta® membranes (ionic and non-ionic) manufactured by Tokuyama, Aciplex® membranes, SelemLon® membranes, and Flemion membranes (all of which are available as ionic and non-ionic) from Asahi Corporation, Raipare™ membranes from Pall Gellman Sciences Corporation, and C-class membranes from Solvay Corporation.

Figure 2:
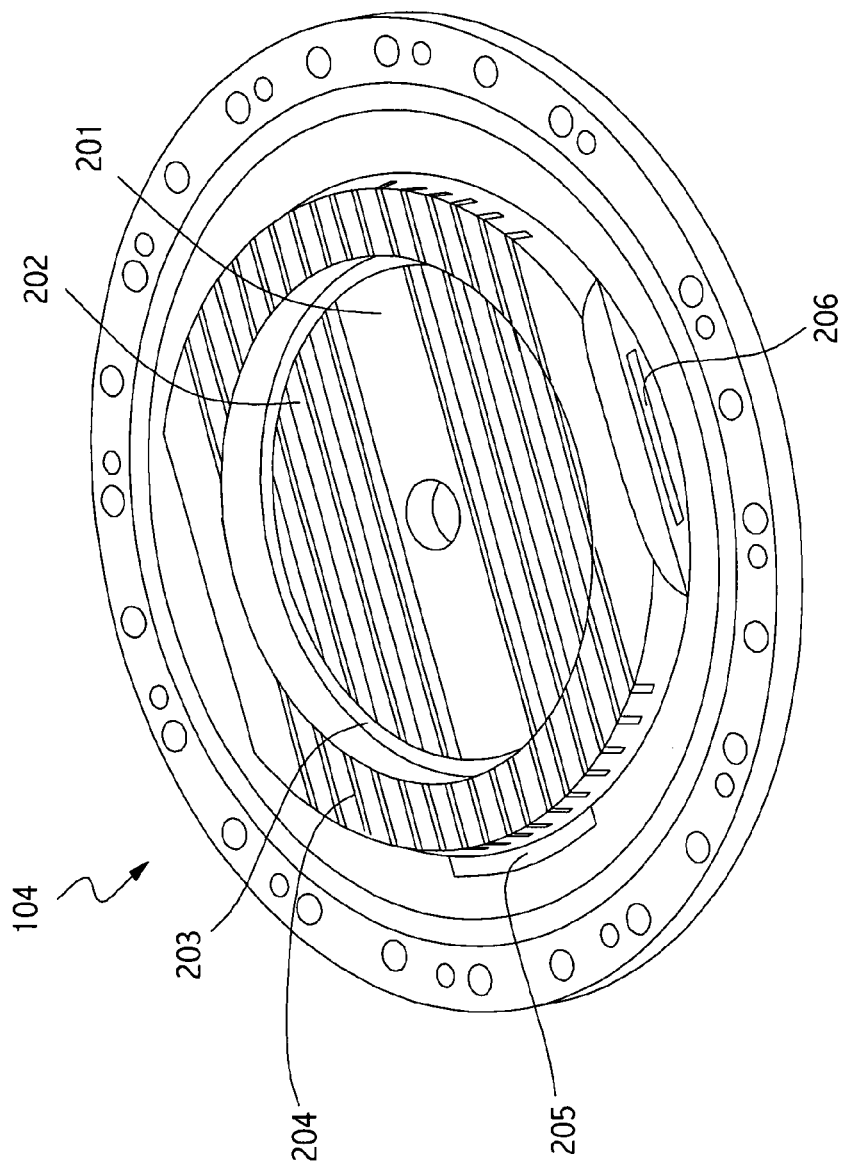
FIG. 2 illustrates a perspective view of an anode base plate of the invention.

FIG. 2 illustrates a perspective view of base member 104. The upper surface of the base member 104 generally includes an annular recess region 201 configured to receive the anode 105 therein. Further, the surface of the annular recess region 201 generally includes a plurality of channels 202 formed therein. Each of the channels 202 are generally positioned in parallel orientation with each other and terminate at the periphery of the annular recessed region 201. Additionally, the periphery of the annular recess region 201 also includes an annular drain channel 203 that extends around the perimeter of the annular recess region 201. Each of the plurality of the parallel positioned channels 202 terminate at opposing ends into the annular drain channel 203. Therefore, the channels 202 may receive dense fluids from anode slots 302 and transmit the dense fluids to a the annular drain channel 203 via the channels 202. The vertical wall that defines the annular recess region 201 generally includes a plurality of slots 204 formed into the wall. The slots 204 are generally positioned in parallel orientation with each other, and further, are generally positioned in parallel orientation with the plurality of the channels 202 formed into the lower surface of the annular recess region 201. The base member 104 also includes at least one fluid supply conduit 205 configured to dispense a fluid into the anode region of the plating cell 100, along with at least one plating solution supply conduit 206 that is configured to dispense a plating solution into the cathode compartment of the plating cell 100. The respective supply conduits 205 and 206 are generally in fluid communication with at least one fluid 109 positioned on a lower surface of the base member 104, as illustrated in FIG. 1. The base member 104 generally includes a plurality of conduits formed therethrough (not shown), wherein the conduits are configured to direct fluids received by individual fluid inlets/drain 109 to the respective cathode and anode chambers of the plating cell 100.

Figure 3:
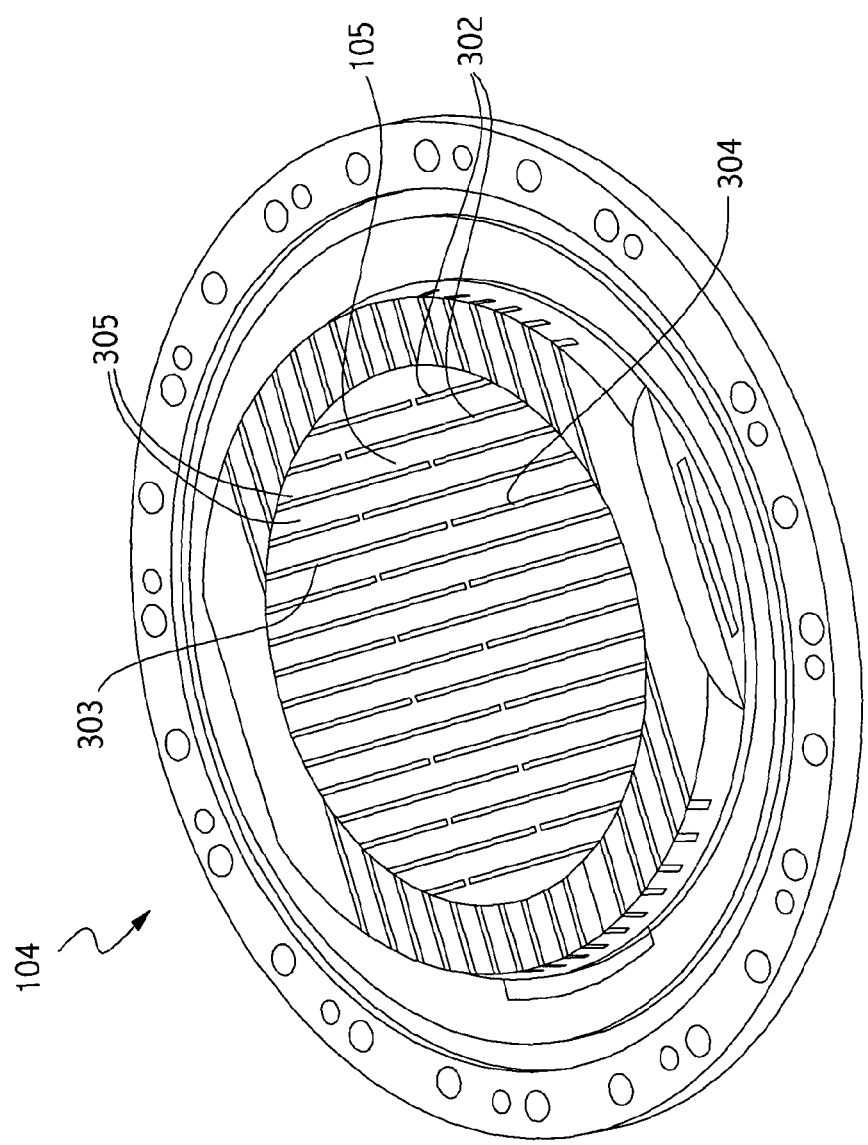
FIG. 3 illustrates a perspective view of an exemplary anode base plate of the invention having an anode positioned therein.
Figure 4:
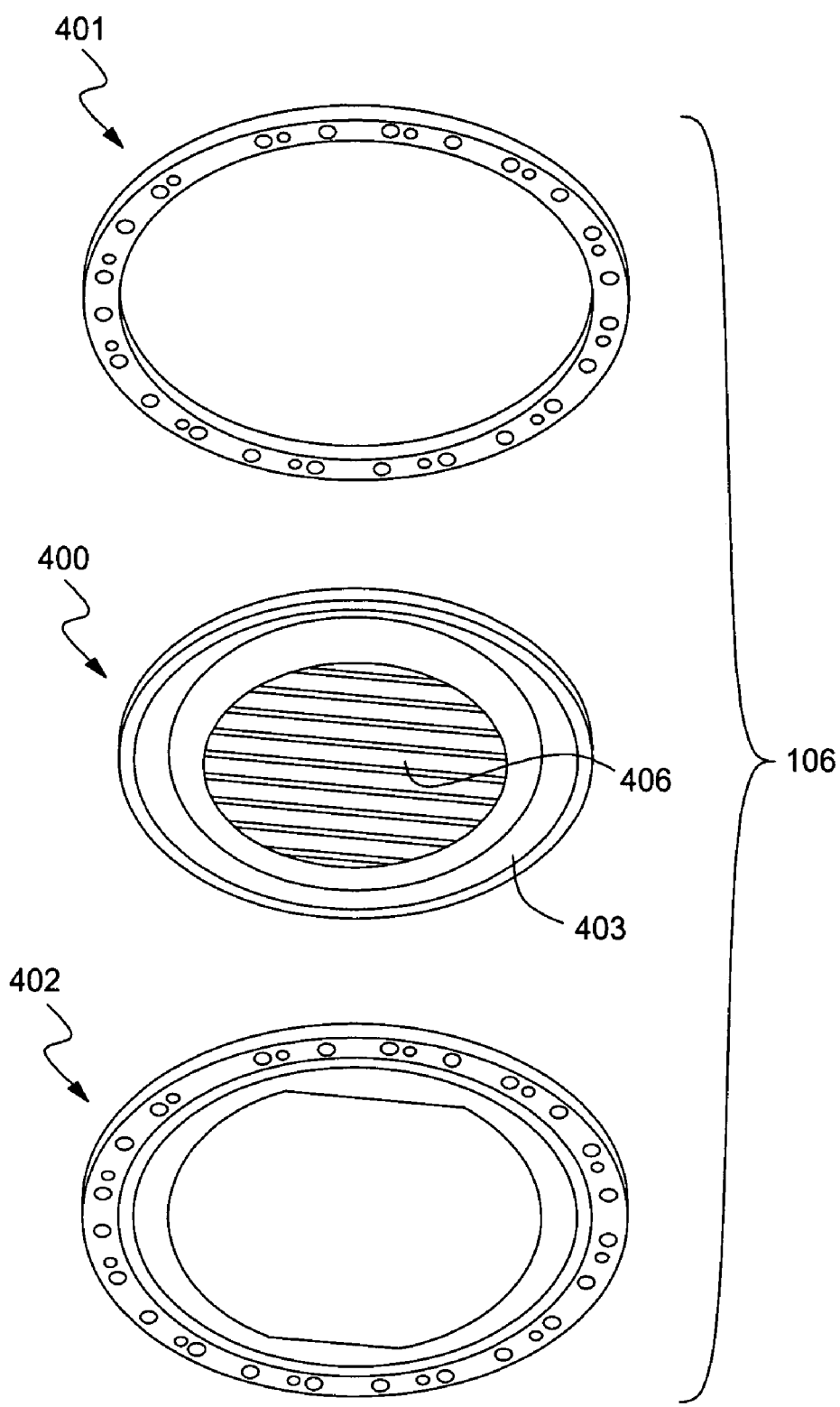
FIG. 4 illustrates an exploded perspective view of an exemplary membrane support member of the invention.

FIG. 3 illustrates a perspective view of the base member 104 having the disk shaped anode 105 positioned therein. The anode 105, which is generally a disk shaped copper member, i.e., a soluble-type copper anode generally used to support copper electrochemical plating operations, generally includes a plurality of anode slots 302 formed therein. The anode slots 302 generally extend through the interior of the anode 105 and are in fluid communication with both the upper surface and lower surface of anode 105. As such, the anode slots 302 allow fluids to travel through the interior of the anode 105 from the upper surface to the lower surface. The anode slots 302 are positioned in parallel orientation with each other. However, when the anode 105 is positioned within the annular recess region 201 of the base member 104, the parallel anode slots 302 of the anode 105 are generally positioned orthogonal to both the slots 204 and the channels 202 of the base member 104, as illustrated cooperatively by FIGS. 2 and 3. Additionally, the anode slots 302 generally do not continuously extend across the upper surface of the anode 105. Rather, the anode slots 302 are broken into a longer segment 303 and a shorter segment 304, with a space 305 between the two segments, which operates to generate a longer current path through the anode 105 from one side to the other. Further, adjacently positioned anode slots 302 have the space 305 positioned on opposite sides of the anode upper surface. The current path from the lower side of the anode 105 to the upper side of the anode 105 generally includes a back and forth type path between the respective anode slots 302 through the spaces 305. Further, the positioning of the spaces 305 and the anode slots 302 provides for improved concentrated Newtonian fluid removal from the surface of the anode 105, as the positioning of the anode slots 302 provides a shortest possible distance of travel for the dense fluids to be received in the anode slots 302. This feature is important, as dense fluids generally travel slowly, and therefore, it is desirable FIG. 4 illustrates an exploded perspective view of an exemplary membrane support assembly 106 of the invention. The membrane support assembly 106 generally includes an upper ring shaped support member 401, an intermediate membrane support member 400, and a lower support member 402. The upper and lower support members 401 and 402 are generally configured to provide structural support to the intermediate membrane support member 400, i.e., the upper support member 401 operates to secure the intermediate membrane support member 400 to the lower support member 402, while the lower support member 402 receives the intermediate membrane support member 400. The intermediate membrane support member 400 generally includes a substantially planar upper surface having a plurality of bores partially formed therethrough. A lower surface of the intermediate membrane support member 400 generally includes a tapered outer portion 403 and a substantially planar inner membrane engaging surface 406. An upper surface of the lower support member 402 may include a corresponding tapered portion configured to receive the tapered outer portion 403 of the intermediate membrane support member 400 thereon. The membrane engaging surface 406 generally includes a plurality of parallel positioned/orientated channels (not shown). Each of the channels formed into the lower surface of the intermediate membrane support member 400 are in fluid communication with at least one of the plurality of bores partially formed through the planar upper surface of the intermediate membrane support member 400. The channels operate to allow a the membrane 112 positioned in the membrane support assembly 106 to deform slightly upward in the region of the channels, which provides a flow path for air bubbles and less dense fluids in the cathode chamber to travel to the perimeter of the membrane 112 and be evacuated from the anode chamber.

In operation, the plating cell 100 of the invention provides a small volume (electrolyte volume) processing cell that may be used for copper electrochemical plating processes, for example. Plating cell 100 may be horizontally positioned or positioned in a tilted orientation, i.e., where one side of the cell is elevated vertically higher than the opposing side of the cell, as illustrated in FIG. 1. If plating cell 100 is implemented in a tilted configuration, then a tilted head assembly and substrate support member may be utilized to immerse the substrate at a constant immersion angle, i.e., immerse the substrate such that the angle between the substrate and the upper surface of the electrolyte does not change during the immersion process. Further, the immersion process may include a varying immersion velocity, i.e., an increasing velocity as the substrate becomes immersed in the electrolyte solution. The combination of the constant immersion angle and the varying immersion velocity operates to eliminate air bubbles on the substrate surface.

Assuming a tilted implementation is utilized, a substrate is first immersed into a plating solution contained within the inner basin 102. Once the substrate is immersed in the plating solution, which generally contains copper sulfate, chlorine, and one or more of a plurality of organic plating additives (levelers, suppressors, accelerators, etc.) configured to control plating parameters, an electrical plating bias is applied between a seed layer on the substrate and the anode 105 positioned in a lower portion of the plating cell 100. The electrical plating bias generally operates to cause metal ions in the plating solution to deposit on the cathodic substrate surface. The plating solution supplied to the inner basin 102 is continually circulated through the inner basin 102 via the fluid inlets/drains 109. More particularly, the plating solution may be introduced in the plating cell 100 via a the fluid inlet/drains 109. The solution may travel across the lower surface of the base member 104 and upward through one of the fluid apertures/conduits 206. The plating solution may then be introduced into the cathode chamber via a channel formed into the plating cell 100 that communicates with the cathode chamber at a point above the membrane support assembly 106. Similarly, the plating solution may be removed from the cathode chamber via a fluid drain positioned above the membrane support assembly 106, where the fluid drain is in fluid communication with one of the fluid inlets/drains 109 positioned on the lower surface of the base member 104. For example, the base member 104 may include first and second fluid apertures 206 positioned on opposite sides of the base member 104. The oppositely positioned fluid apertures 206 may operate to individually introduce and drain the plating solution from the cathode chamber in a predetermined direction, which also allows for flow direction control. The flow control direction provides control over removal of light fluids at the lower membrane surface, removal of bubbles from the anode chamber, and assists in the removal of dense or heavy fluids from the anode surface via the channels 202 formed into the base member 104.

Once the plating solution is introduced into the cathode chamber, the plating solution travels upward through a diffusion plate 110. d The diffusion plate 110, which is generally a ceramic or other porous disk shaped member, generally operates as a fluid flow restrictor to even out the flow pattern across the surface of the substrate. Further, the diffusion plate 110 operates to resistively damp electrical variations in the electrochemically active area, the anode or cation membrane surface, which is known to reduce plating uniformities. Additionally, embodiments of the invention contemplate that the ceramic diffusion plate 110 may be replaced by a hydrophilic plastic member, i.e., a treated PE member, an PVDF member, a PP member, or other material that is known to be porous and provide the electrically resistive damping characteristics provided by ceramics. However, the plating solution introduced into the cathode chamber, which is generally a plating catholyte solution, i.e., a plating solution with additives, is not permitted to travel downward through the membrane 112 positioned on the lower surface 404 of the membrane support assembly 106 into the anode chamber, as the anode chamber is fluidly isolated from the cathode chamber by the membrane 112. The anode chamber includes separate individual fluid supply and drain sources configured to supply an anolyte solution to the anode chamber. The solution supplied to the anode chamber, which may generally be copper sulfate in a copper electrochemical plating system, circulates exclusively through the anode chamber and does not diffuse or otherwise travel into the cathode chamber, as the membrane 112 positioned on the membrane support assembly 106 is not fluid permeable in either direction.

Additionally, the flow of the fluid solution (anolyte, i.e., a plating solution without additives, which may be referred to as a virgin solution) into the anode chamber is directionally controlled in order to maximize plating parameters. For example, anolyte may be communicated to the anode chamber via an individual fluid inlet ofthe fluid inlets/drains 109. The individual fluid inlet is in fluid communication with a fluid channel formed into a lower portion of the base member 104 and the fluid channel communicates the anolyte to one of fluid supply conduits 205. A seal positioned radially outward of the fluid supply conduits 205, in conjunction with the surrounding structure, directs the anolyte flowing out of the fluid supply conduits 205 upward and into the slots 204 (also termed channels). Thereafter, the anolyte generally travels across the upper surface of the anode 105 towards the opposing side of the base member 104, which in a tilted configuration, is generally the higher side of the plating cell 100. The anolyte travels across the surface of the anode 105 below the membrane positioned 112 immediately above. Once the anolyte reaches the opposing side of the anode 105, it is received into a corresponding fluid channel 204 and drained from the plating cell 100 for recirculation thereafter.

During plating operations, the application of the electrical plating bias between the anode 105 and the cathode generally causes a breakdown of the anolyte solution contained within the anode chamber. More particularly, the application of the plating bias operates to generate multiple hydrodynamic or Newtonian layers of the copper sulfate solution within the anode chamber. The hydrodynamic layers generally include a layer of concentrated copper sulfate positioned proximate the anode 105, an intermediate layer of normal copper sulfate, and a top layer of lighter and depleted copper sulfate proximate the membrane. The depleted layer is generally a less dense and lighter layer of copper sulfate than the copper sulfate originally supplied to the anode compartment, while the concentrated layer is generally a heavier and denser layer of copper sulfate having a very viscous consistency. The dense consistency of the concentrated layer proximate the anode causes electrical conductivity problems (known as anode passivation) in anodes formed without the anode slots 302. However, the anode slots 302, in conjunction with the tilted orientation of the plating cell 100, operate to receive the concentrated viscous layer of copper sulfate and remove the layer from the surface of the anode, which eliminates conductivity variances. Further, the plating cell 100 generally includes one side that is tilted upward or vertically positioned above the other side, and therefore, the surface of ther anode 105 is generally a plane that is also tilted. The tilt causes the layer of concentrated copper sulfate generated at the surface of the anode to generally flow downhill as a result of the gravitational force acting thereon. As the concentrated copper sulfate layer flows downhill, it is received within one of the anode slots 302 and removed from the surface of the anode 105. As discussed above, the anode slots 302 are generally parallel to each other and are orthogonal to the slots 204. Therefore, the anode slots 302 are also orthogonal to the channels 202 formed into the lower surface of the base member 104. As such, each of the anode slots 302 finally intersects several of the channels 202. This configuration allows the concentrated copper sulfate received within the anode slots 302 to be communicated to one or more of the channels 202. Thereafter, the concentrated copper sulfate may be communicated via the channels 202 to the annular drain 203 positioned within the recessed portion 201. The drain 203 in communication with the channels 202 may generally be communicated through the base member 104 and back to a central anolyte supply tank, where the concentrated copper sulfate removed from the anode surface may be recombined with a volume of stored copper sulfate used for the anolyte solution.

Figure 5:
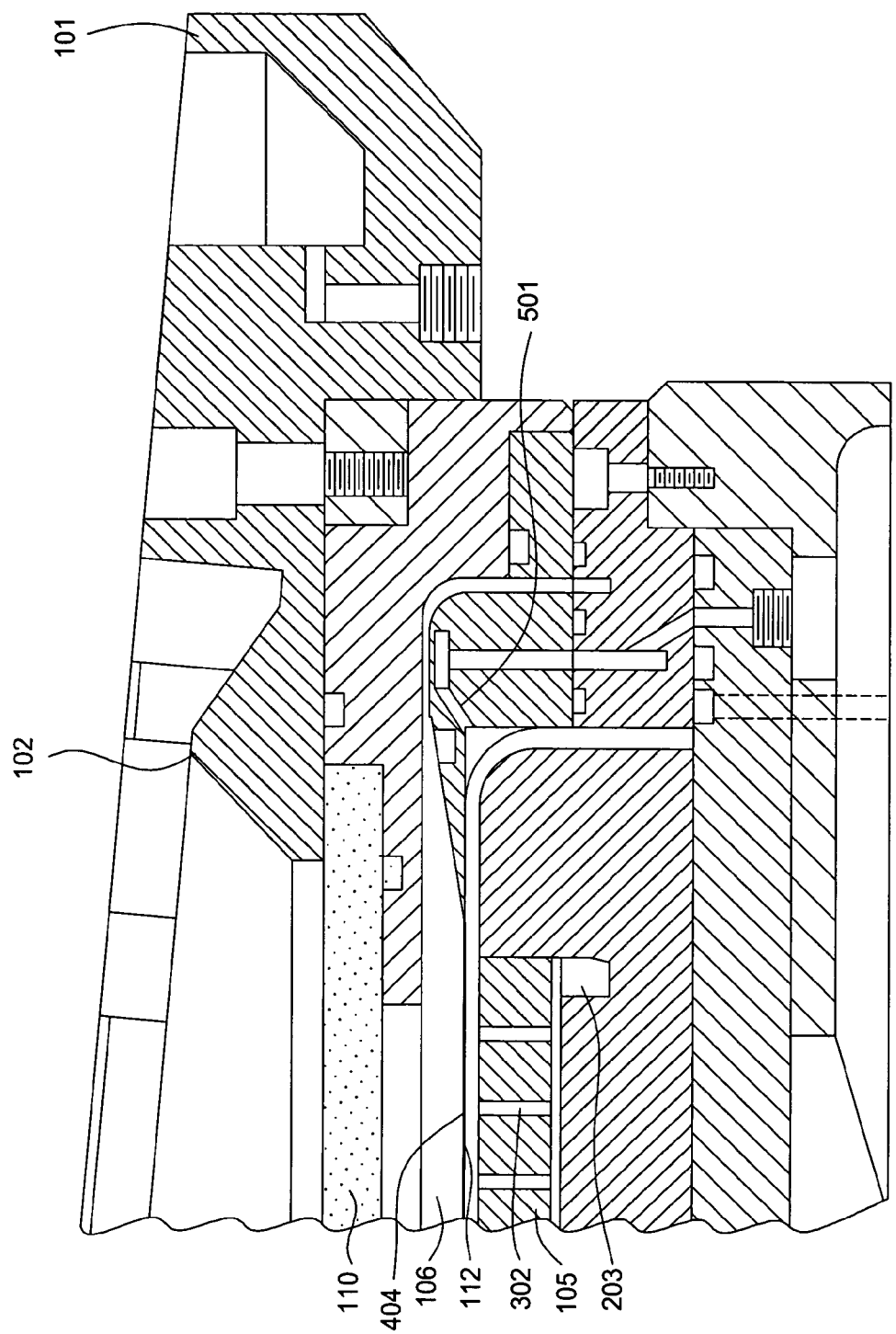
FIG. 5 illustrates a partial sectional view of an edge of the plating cell of the invention.

Similarly, the upper portion of the anode chamber generates a diluted layer of copper sulfate proximate the membrane. The diluted layer of copper sulfate may be removed from the anode chamber via an air vent 501, as illustrated in FIG. 5. Air vent/drain 501, which may include multiple ports, is generally positioned on the upper side of the electrochemical plating cell 100, and therefore, is positioned to receive both bubbles trapped within the anode chamber, as well as the diluted copper sulfate generated at the membrane surface. The air vents 501 are generally in fluid communication with the anolyte tank discussed above, and therefore, communicates the diluted copper sulfate received therein back to the anolyte tank, where the diluted copper sulfate may combine with the concentrated copper sulfate removed via the anode slots 302 to form the desired concentration of copper sulfate within the anolyte tank. Any bubbles trapped by the air vent 501 may also be removed from the cathode chamber vented to atmosphere or simply maintained within the anolyte tank and not recirculated into the cathode chamber.

The catholyte solution (the solution used to contact and plate metal/copper onto the substrate) generally includes several constituents. The constituents generally include a virgin makeup plating solution (a plating solution that does not contain and plating additives, such as levelers, suppressors, or accelerators, such as that provided by Shipley Ronal of Marlborough, Mass. or Enthone, a division of Cookson Electronics PWB Materials & Chemistry of London), water (generally included as part of the VMS, but is may also be added), and a plurality of plating solution additives configured to provide control over various parameters of the plating process. The catholyte is generally a low acid-type of plating solution, i.e., the catholyte generally has between about 5 g/L of acid and about 50 g/L of acid, or more particularly, between about 5 g/L and about 10 g/L. The acid may be sulfuric acid, sulfonic acid (including alkane sulfonic acids), pyrophosphoric acid, citric acid, and other acids known to support electrochemical plating processes. The desired copper concentration in the catholyte is generally between about 25 g/L and about 70 g/L, preferably between about 30 g/L and about 50 g/L of copper. The copper is generally provided to the solution via copper sulfate, and/or through the electrolytic reaction of the plating process wherein copper ions are provided to the solution via the anolyte from a soluble copper anode positioned in the catholyte solution. More particularly, copper sulfate pentahydrate ($CuSO_4.5H_2O$) may be diluted to obtain a copper concentration of about 40 g/L, for example. A common acid and copper source combination is sulfuric acid and copper sulfate, for example. The catholyte also has chloride ions, which may be supplied by hydrochloric acid or copper chloride, for example, and the concentration of the chloride may be between about 30 ppm and about 60 ppm.

As noted above, the plating solution (catholyte) generally contains one or more plating additives configured to provide a level of control over the plating process. The additives may include suppressors at a concentration of between about 1.5 mL/L and about 4 mL/L, preferably between about 2 mL/L and 3.0 mL/L. Exemplary suppressors include ethylene oxide and propylene oxide copolymers. Additives may also include accelerators at a concentration of between about 3 mL/L and about 10 mL/L, preferably within the range of between about 4.5 mL/L and 8.5 mL/L. Exemplary accelerators are based on sulfopropyl-disulfide or mercaptopropane-sulphonate and their derivatives. Additionally, another additive that may optionally be added to the catholyte solution is a leveler at a concentration of between about 1 mL/L and about 12 mL/L, or more particularly, in the range of between about 1.5 mL/L and 4 mL/L The anolyte solution, as noted above, is generally contained in the volume below the membrane and above the anode. The anolyte solution may be simply the catholyte solution without the plating additives, i.e., levelers, suppressors, and/or accelerators. However, the inventors have found that specific anolyte solutions, other than just stripped catholyte solutions, provide a substantial improvement in plating parameters. Specifically, copper transfer through the membrane and prevention of copper sulfate and hydroxide precipitation, i.e., when the Cu ions transport through membrane, copper sulfate accumulates in the anolyte and starts to precipitate on the anode provoking its passiviation are improved. When pH of the anolyte is maintained above about 4.5 to about 4.8, copper hydroxide starts to deposit from Cu salt solutions, i.e., $Cu_2{++}2H_2O = Cu(OH)_2$(deposit)$+2H^+$. More particularly, the inventors have found that if the anolyte can be configured to supply between about 90% and about 100% of the copper to the catholyte, then the membrane essentially operates as a clean copper anode, i.e., the membrane provides copper to the catholyte without the disadvantages associated with the electrochemical reaction that takes place at the surface of the anode (sludge formation, additive consumption, planarity variations due to erosion, etc.). The anolyte of the invention generally includes a soluble copper II salt (copper ions are not complexed with ligands like $NH_3$, or EDTA or phyrophoshoric acid anions, as Cu transports through the membrane together with this ligand, like Cu(NH3)4 2+ will transport together with $NH_3$, such as copper sulfate, copper sulfonate, copper chloride, copper bromide, copper nitrate, or a blend of any combination of these salts in an amount sufficient to provide a concentration of copper ions in the catholyte of between about 0.1M and about 2.5M, or more particularly, between about 0.25 M and about 2M.

Additionally, the pH of the anolyte solution will generally be between about 1.5 and about 6, or more particularly, between about 2 and 4.8, for example. The pH is maintained in this range, as increasing the pH above this range in conventional plating configurations has been shown cause copper hydroxide precipitation. Additionally, when the pH is below 2, and particularly if the pH is below 1.5, then the solution supports a substantial increase in the hydrogen ion ($H^+$) transport through the membrane from the anolyte to the catholyte. In this situation, the bulk of the plating current is carried by the $H^+$ ions and the copper ion transport is reduced. As such, the copper ion concentration in the catholyte decreases, potentially to a critical level that will not support plating, while simultaneously the sulfuric acid concentration in the catholyte increases. The anolyte can generally use any soluble $Cu^{2+}$ salt, such as $CuSO_4$ (solubility 300 g/L), $CuBr_2$ (solubility more that 2 kg/L), $CuCl_2$ (solubility 700 g/L), $CuF_2$ (47 g/L), $Cu(NO_3)_2$ (1300 g/L) etc. The selection of anions depends on their impact to prevent or minimize Cu(I) formation and anode passiviation, on penetration through the membrane etc. For instance, the anolyte can be $CuSO_4$ (0.5 M) with small additions of $Cu(NO_3)$ to activate anode surface and minimize Cu(I) formation. To minimize Cu(I) formation, small additions of $Cu(ClO_3)_2$ (solubility 2 kg/L) or $Cu(IO_3)_2$—solubility 1 g/L may be used. In similar fashion to the catholyte, the source of copper in the anolyte (aside from the anode) may be copper sulfate pentahydrate ($CuSO_4.5H_2O$) at between about 51 g/L and 70 g/L, or at between about 0.75 M and about 0.95 M. Alternatively, in a preferred embodiment, the copper source may be between about 51 g/L and about 60 g/L, preferably about 54 g/L, and at a molarity of between about 0.8 M and about 0.9 M, preferably about 0.85M.

While the foregoing is directed to embodiments of the present invention, other and further embodiments of the invention may be devised without departing from the basic scope thereof, and the scope thereof is determined by the claims that follow

The invention claimed is:

1. A method for plating metal onto a substrate, comprising:
positioning the substrate in a catholyte solution contained in a catholyte chamber of a plating cell, the catholyte solution comprising:
an acid source at a concentration of between about 5 g/L and about 15 g/L;
a copper source at a concentration of between about 0.8M and about 0.9M;
chlorine ions at a concentration of between about 25 ppm and about 75 ppm; and
one or more additives; and
applying a plating bias between the substrate and an anode positioned in an anolyte chamber of the plating cell, the anolyte chamber being separated from the catholyte chamber by an ionic membrane and being supplied with an anolyte solution comprising a copper source having a concentration of greater than about 51 g/L, wherein the anolyte solution does not contain the one or more additives.

2. The method of claim 1, wherein the one or more additives in the catholyte solution comprises:
a leveler at a concentration of between about 2 mL/L and about 3 mL/L;
a suppressor at a concentration of between about 2 mL/L and about 3 mL/L; and
an accelerator at a concentration of between about 5.5 mL/L and about 8 mL/L.

3. The method of claim 2, wherein the suppressor comprises a compound selected from the group consisting of ethylene oxide, propylene oxide, and combinations thereof.

4. The method of claim 2, wherein the accelerator comprises sulfo propyldisulfide.

5. The method of claim 1, wherein the anolyte has a pH of between about 2 and about 4.8.

6. The method of claim 5, wherein the anolyte comprises a copper II salt having a concentration of copper ions of between about 0.1M and about 2M.

7. The method of claim 6, wherein the copper II salt comprises a compound selected from the group consisting of copper sulfate, copper sulfonate, copper chloride, copper nitrate, and blends thereof.

8. The method of claim 5, wherein the anolyte provides a copper transport of copper ions through the ionic membrane of between about 90% and about 100%.

9. The method of claim 1, wherein the anode is selected from the group consisting of a copper anode, a platinum anode, and combinations thereof.

10. A method for plating copper into features formed on a semiconductor substrate, comprising:
positioning the substrate in a plating cell, wherein the plating cell comprises:
a catholyte volume containing a catholyte solution;
an anolyte volume containing an anolyte solution, wherein the difference between the catholyte solution and the anolyte solution is that the catholyte solution comprises one or more additives;
an ionic membrane positioned to separate the anolyte volume from the catholyte volume; and
an anode positioned in the anolyte volume;
applying a plating bias between the anode and the substrate;
plating copper ions onto the substrate from the catholyte solution; and
replenishing the copper ions plated onto the substrate from the catholyte solution with copper ions transported from the anolyte solution via the ionic membrane, wherein the anolyte solution has a copper concentration of greater than about 51 g/L.

11. The method of claim 10, wherein the copper concentration is supplied by copper sulfate pentahydrate having a molarity of between about 0.8M and about 0.9M.

12. The method of claim 11, wherein the anolyte solution has a pH of between about 2 and 4.8.

13. The method of claim 10, wherein the plating cell further comprises a diffusion member positioned between an upper surface of the ionic membrane and the substrate.

14. The method of claim 13, wherein the diffusion member comprises a porous ceramic disk.

15. The method of claim 10, wherein the ionic membrane comprises a membrane having a fluorized polymer matrix.

16. The method of claim 10, wherein the ionic membrane comprises a membrane having a polydivnilbenzol matrix.

17. The method of claim 12, wherein the catholyte solution comprises:
  acid at a concentration of between about 5 g/L and about 15 g/L;
  copper at a concentration of between about 0.8M and about 0.9M; and
  chlorine ions at a concentration of between about 25 ppm and about 75 ppm.

18. The method of claim 17, wherein the one or more additives in the catholyte solution further comprises:
  a leveler at a concentration of between about 2 mL/L and about 3 mL/L;
  a suppressor at a concentration of between about 2 mL/L and about 3 mL/L; and
  an accelerator at a concentration of between about 5 mL/L and about 8 mL/L.

19. A method for electrochemically plating copper onto features of a semiconductor substrate, comprising:
  positioning the substrate in a plating cell having a catholyte solution volume, an anolyte solution volume, and an ionic membrane separating catholyte solution volume from the anolyte solution volume;
  contacting the substrate with a catholyte solution;
  applying an electrical bias between the substrate and an anode positioned in the anolyte volume, the electrical bias being sufficient to plate copper ions from the catholyte solution onto the substrate; and
  replenishing copper ions plated from the catholyte solution via transfer of copper ions from an anolyte solution through the ionic membrane to the catholyte solution, the anolyte solution having a pH of between about 2 and about 4.8 and a copper ion concentration of between about 0.1M and about 2M, wherein the difference between the catholyte solution and the anolyte solution is that the catholyte solution comprises one or more additives.

20. The method of claim 19, wherein the copper ion concentration in the anolyte comprises between about 51 g/L and about 60 g/L of copper metal to the anolyte.

21. The method of claim 19, wherein the anolyte provides a copper transport of copper ions through the ionic membrane of between about 90% and about 100%.

22. The method of claim 19, wherein the catholyte solution volume comprises:
  an acid source at a concentration of between about 5 g/L and about 15 g/L;
  a copper source at a concentration of between about 0.8M and about 0.9M; and
  chlorine ions at a concentration of between about 25 ppm and about 75 ppm.

23. The method of claim 22, wherein the one or more additives in the catholyte further comprises:
  a leveler at a concentration of between about 2 mL/L and about 4 mL/L;
  a suppressor at a concentration of between about 1.5 mL/L and about 3 mL/L; and
  an accelerator at a concentration of between about 5.5 mL/L and about 8 mL/L.

24. The method of claim 23, wherein the anode is selected from the group consisting of a copper anode, a platinum anode, and combinations thereof.

25. A method for plating copper onto a substrate, comprising:
  positioning the substrate in a catholyte plating solution contained in a catholyte chamber of a plating cell, the catholyte plating solution comprising:
    an acid source at a concentration of between about 5 g/L and about 15 g/L;
    a copper source at a concentration of between about 0.5M and about 1.0M;
    chlorine ions at a concentration of between about 25 ppm about 75 ppm; and
    one or more additives; and
  applying a plating bias between the substrate and an anode positioned in an anolyte chamber of the plating cell, the anolyte chamber being separated from the catholyte chamber by an ionic membrane, wherein the difference between the catholyte solution and the anolyte solution is that the catholyte solution comprises the one or more additives.

26. The method of claim 25, wherein the anolyte comprises a copper source having a concentration of greater than about 51 g/L.

27. The method of claim 26, wherein the anolyte has a pH of between about 2 and about 4.8.

28. The method of claim 26, wherein the ionic membrane comprises a membrane having a polydivinilbenzol matrix.

29. A method for plating metal onto a substrate, comprising:
  positioning the substrate in a catholyte solution contained in a catholyte chamber of a plating cell, the catholyte solution comprising a copper source at a concentration of between about 0.8M and about 0.9M and one or more additives; and
  applying a plating bias between the substrate and an anode positioned in an anolyte chamber of the plating cell, the anolyte chamber being separated from the catholyte chamber by an ionic membrane and being supplied with an anolyte solution comprising a copper source at a concentration of greater than about 51 g/L, wherein the ionic membrane is positioned at a vertical position above the anode and in substantially parallel relationship to an upper surface of the anode.

30. The method of claim 29, wherein the ionic membrane comprises a membrane having a polydivinilbenzol matrix.

31. The method of claim 29, wherein the upper surface of the anode is tilted between about 3° and about 30° from horizontal.

* * * * *

UNITED STATES PATENT AND TRADEMARK OFFICE
CERTIFICATE OF CORRECTION

PATENT NO. : 7,128,823 B2
APPLICATION NO. : 10/616044
DATED : October 31, 2006
INVENTOR(S) : Yang et al.

It is certified that error appears in the above-identified patent and that said Letters Patent is hereby corrected as shown below:

Column 2, Line 10: Delete the comma after "operates"

Column 3, Line 22: Delete the second instance of "and about"

Column 6, Line 39: Change "ph" to --pH--

Column 7, Line 55: Before "the", delete "a"

Column 8, Line 2: After "fluid", insert --inlets/drains--

Column 8, Line 7: Change "drain" to --drains--

Column 8, Line 14: Before "anode", insert --the--

Column 8, Line 17: Before "anode", insert --the--

Column 8, Line 44: Insert a period after "desirable"

Column 9, Line 6: After "allow", delete "a"

Column 9, Line 48: Before "the", delete "a"

Column 9, Line 48: Change "inlet" to --inlets--

Column 10, Line 6: Delete "d"

Column 10, Line 53: Change "positioned 112" to --112 positioned--

UNITED STATES PATENT AND TRADEMARK OFFICE
CERTIFICATE OF CORRECTION

PATENT NO.       : 7,128,823 B2
APPLICATION NO.  : 10/616044
DATED            : October 31, 2006
INVENTOR(S)      : Yang et al.

It is certified that error appears in the above-identified patent and that said Letters Patent is hereby corrected as shown below:

Column 10, Line 56: Delete "204"

Column 11, Line 16: Change "ther" to --the--

Column 11, Line 63: Delete "and"

Column 12, Line 40: Insert a period at the end of the paragraph

Column 12, Line 66: Change "phyrophoshoric" to --pyrophosphoric--

Column 13, Line 1: Change "Cu(NH3)4 2+" to --$Cu(NH_3)_4^{2+}$--

Column 13, Line 12: After "shown", insert --to--

Column 13, Line 23: Change "$Cu^2+$" to --$Cu^{2+}$--

Column 13, Line 45: Insert a period at the end of the paragrph

Column 14, Claim 16, Line 67: Change "polydivnilbenzol" to --polydivinilbenzol--

Column 16, Claim 25, Line 17: Change "ppm about" to --ppm and about--

Signed and Sealed this

Thirteenth Day of March, 2007

JON W. DUDAS
*Director of the United States Patent and Trademark Office*